United States Patent [19]

Clement et al.

[11] Patent Number: 5,203,769

[45] Date of Patent: * Apr. 20, 1993

[54] MEDICAL DEVICE VALVING MECHANISM

[75] Inventors: Thomas P. Clement; David P. Weber, both of Bloomington, Ind.

[73] Assignee: Mectra Labs, Inc., Bloomfield, Ind.

[ * ] Notice: The portion of the term of this patent subsequent to May 28, 2008 has been disclaimed.

[21] Appl. No.: 660,356

[22] Filed: Feb. 22, 1991

Related U.S. Application Data

[63] Continuation-in-part of Ser. No. 432,084, Nov. 6, 1989, Pat. No. 5,019,054.

[51] Int. Cl.⁵ ............................................. A61M 5/00
[52] U.S. Cl. ...................................... 604/32; 604/35; 604/43; 604/248; 604/902; 251/309
[58] Field of Search .................. 604/30, 35, 32, 43, 604/246, 248, 902; 251/209, 231, 309, 312, 340; 137/595, 625.19, 625.23, 625.47, 626, 862

[56] References Cited

U.S. PATENT DOCUMENTS

| | | |
|---|---|---|
| 628,907 | 7/1899 | Hart . |
| 786,215 | 3/1905 | Hepnar . |
| 811,111 | 1/1906 | Wegefarth . |
| 1,658,754 | 2/1928 | Wood . |
| 2,812,765 | 11/1957 | Tofflemire ................ 604/902 |
| 3,012,752 | 12/1961 | Buck . |
| 3,048,192 | 8/1962 | Murphy, Jr. . |
| 3,081,770 | 3/1963 | Hunter . |
| 3,157,201 | 11/1964 | Littmann . |
| 3,434,691 | 3/1969 | Hamilton . |
| 3,467,082 | 9/1969 | Gilbert . |
| 3,783,900 | 1/1974 | Waldbillig . |
| 3,788,602 | 1/1974 | Kitzie . |
| 3,794,032 | 2/1974 | Derouineau . |
| 3,833,000 | 9/1974 | Bridgman . |
| 3,834,372 | 9/1974 | Turney . |
| 3,957,082 | 5/1976 | Fuson et al. . |
| 4,079,737 | 3/1978 | Miller . |
| 4,173,328 | 11/1979 | Karbo . |
| 4,230,128 | 10/1980 | Aramayo . |
| 4,280,498 | 7/1981 | Jensen . |
| 4,282,873 | 8/1981 | Roth . |
| 4,299,217 | 11/1981 | Sagae et al. . |
| 4,314,586 | 2/1982 | Folkman . |
| 4,397,335 | 8/1983 | Doblar et al. . |
| 4,487,600 | 12/1984 | Brownlie et al. .............. 604/35 |
| 4,540,156 | 9/1985 | Cross . |
| 4,553,964 | 11/1985 | Sasaki . |
| 4,566,480 | 1/1986 | Parham . |
| 4,568,332 | 2/1986 | Shippert . |
| 4,581,014 | 4/1986 | Millerd et al. . |
| 4,593,717 | 6/1986 | Levasseur . |
| 4,595,005 | 6/1986 | Jinotti . |
| 4,605,396 | 8/1986 | Tseo et al. . |

(List continued on next page.)

FOREIGN PATENT DOCUMENTS 3528656 7/1986 Fed. Rep. of Germany .
991478 5/1965 United Kingdom .

*Primary Examiner*—Stephen C. Pellegrino
*Assistant Examiner*—Ralph A. Lewis
*Attorney, Agent, or Firm*—Barnes & Thornburg

[57] ABSTRACT

A medical device valving mechanism comprising an elongated valve body molded to have a longitudinally extending body shaped to be gripped and securely held in either hand leaving the hand's thumb free for valve operational movement. The body has at least one fluid passageway extending longitudinally therethrough and a cylindrical opening extending transversely therethrough to intercept the at least one passageway. A cylindrical molded plastic, one-piece rotor for snug slidable and rotational insertion into the cylindrical opening to block the at least one passageway is provided. The rotor has at least one transaxial passageway which opens the at least one fluid passageway through the valve body when the rotor is in its valve opening position and which closes the at least one fluid passageway when the rotor is in its valve closing position. A thumb-actuated means is provided for rotating the rotor, the actuated means is disposed above the valve body and the rotor for convenient thumb movement. Fluid is directed to or withdrawn from a desired area through a conduit piece attached to the valve body in fluid communication with the transaxial passageway.

14 Claims, 5 Drawing Sheets

U.S. PATENT DOCUMENTS

| | | | |
|---|---|---|---|
| 4,619,643 | 10/1986 | Bai | 604/43 |
| 4,642,097 | 2/1987 | Siposs . | |
| 4,645,496 | 2/1987 | Oscarsson . | |
| 4,648,868 | 3/1987 | Hardwick et al. . | |
| 4,654,027 | 3/1987 | Dragan et al. . | |
| 4,667,927 | 5/1987 | Oscarsson . | |
| 4,680,026 | 7/1987 | Weightman et al. | 604/902 |
| 4,708,717 | 11/1987 | Deane et al. | 604/43 |
| 4,758,235 | 7/1988 | Tu . . | |
| 4,807,666 | 2/1989 | Morse . | |
| 4,911,202 | 3/1990 | Nelson . | |
| 4,925,450 | 5/1990 | Imonti et al. . | |
| 4,941,872 | 7/1990 | Felix et al. | 604/902 |
| 4,964,849 | 10/1990 | Robicsek | 604/902 |
| 4,966,551 | 10/1990 | Betush | 604/32 |
| 5,019,054 | 5/1991 | Clement et al. | 604/248 |

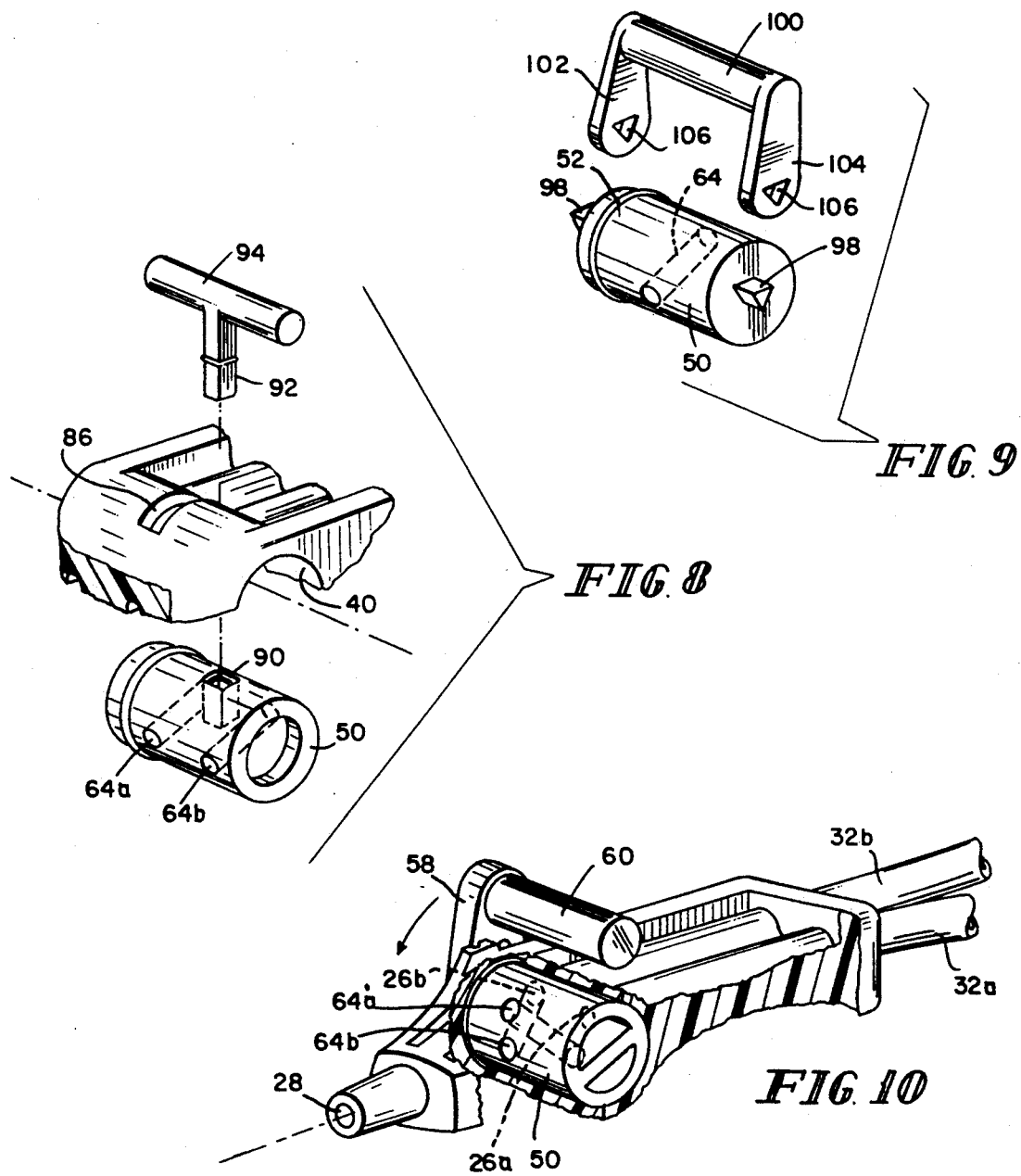

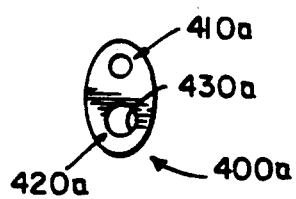
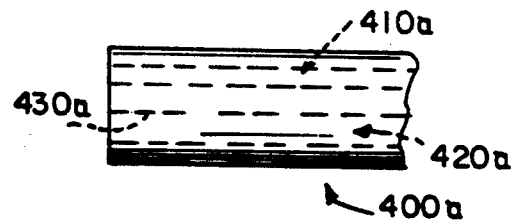
FIG. 16    FIG. 17
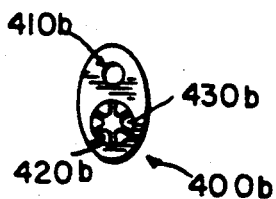
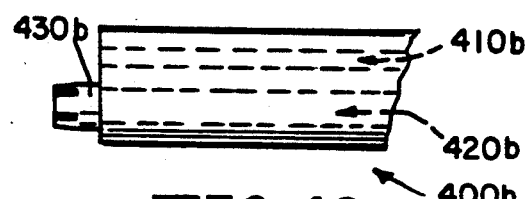
FIG. 18    FIG. 19
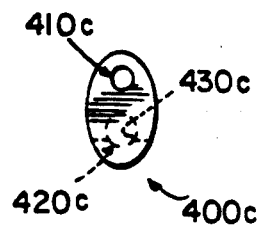
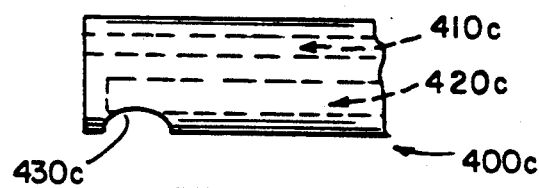
FIG. 20    FIG. 21
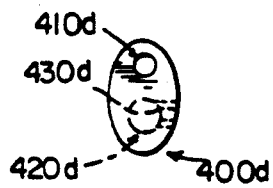
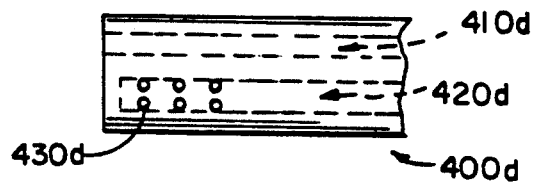
FIG. 22    FIG. 23
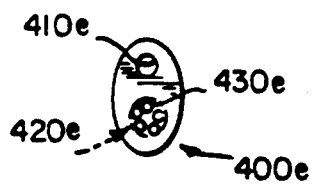
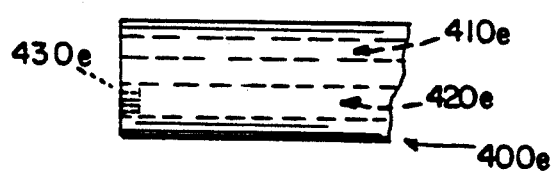
FIG. 24    FIG. 25
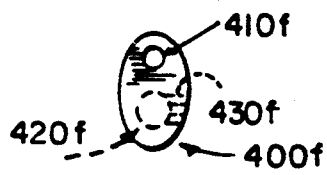
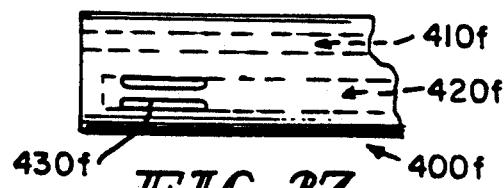
FIG. 26    FIG. 27

5,203,769

MEDICAL DEVICE VALVING MECHANISM

This is a continuation-in-part application of the copending U.S. application "Medical Device Valving Mechanism", U.S. application Ser. No. 07/432,084, now U.S. Pat. No. 5,019,054, filed Nov. 6, 1989.

FIELD OF THE INVENTION

The present invention relates to medical device valving mechanisms and handheld lavages and more particularly to the provision of a valve mechanism which may be held securely in one hand and operated by the thumb of that hand to open and close one or more valve passageways.

BACKGROUND OF THE INVENTION

In recent years, various types of medical procedures have been developed which involve the connection of various fluid tubes between the patient and various instruments including sources of fluid pumped into the patient and suction lines to remove fluid from the patient. All of this development activity has produced a need for a valving mechanism and delivery conduit which can be securely held and controlled by one hand, leaving the other hand free to perform other functions. Since these mechanisms necessarily must be low-cost disposable mechanisms, the conventional prior art designs will not satisfy the requirements for several reasons. The prior art devices are usually too complex and costly to be thrown away when they are contaminated with body fluids. Also, the prior art devices are typically unwieldly and difficult to hold and control with one hand. An example of a prior art medical valve is shown in U.S. Pat. No. 4,568,332 issued to Ronald D. Shippert Feb. 4, 1986. The Shippert valve, which is designed for use in suction lipectomy, is made from metal and is fabricated from a multitude of parts which must be assembled together in a complex assembly system.

BRIEF DESCRIPTION OF THE INVENTION

The medical device valving mechanism of the present invention comprises an elongated valve body molded to have a longitudinal extending body shaped to be gripped and securely held in a user's hand leaving the hand's thumb free for valve operational movement. The valve body provides at least one passageway extending longitudinal therethrough, and also provides a cylindrical opening or rotor bore extending transversely therethrough and intercepting the at least one passageway. A cylindrical molded plastic, one-piece rotor is provided for snug, slidable and rotational insertion into the cylindrical opening to block the said at least one passageway, the rotor being rotatable about its axis between valve opening and valve closing positions. The rotor has at least one transaxially extending passageway therethrough which opens the at least one fluid passageway through the valve body when the rotor is in its valve opening position and which closes the at least one fluid passageway when the rotor is in its valve closing position. The valving mechanism also comprises thumb-actuated means connected to the rotor for rotating the rotor between its positions, the actuating means being disposed above the valve body and the rotor for convenient thumb movement of the rotor. Connected to the valve body in fluid communication with at least one fluid passageway is a conduit piece that channels and directs the flow of fluid leaving or entering the valve body. The conduit piece can be curved with respect to the valve body to extend either upward, downward, or sideways. In certain embodiments the conduit piece can be divided into two or more fluid conduit portions for use with dual valves, and can also extend along a complex curve to direct fluid flow both downward and sideways with respect to the valve body. The conduit piece can be attached to the valve body as an integrally molded piece or separately formed as a snap-on piece that connects in fluid tight communication with the valve body.

The valve body of the present invention is preferably molded to have a forward bottom portion shaped to be gripped by the index finger of one hand and a rearward bottom portion shaped to be gripped by the middle finger of the hand with a depending transverse bottom portion between the forward and rearward portions. The middle transverse bottom portion is preferably directly below the cylindrical opening which holds the rotor to be disposed partially between the index and middle finger for stabilization. Further, the rearward bottom portion is preferably transversely recessed to provide a comfortable gripping surface.

It is an object of the present invention, therefore, to provide a valving mechanism comprising primarily a molded, one-piece plastic valve body and a molded one-piece valve rotor for insertion into the body to complete the valving mechanism. It is another object of the present invention to provide such a mechanism which can be conveniently and comfortably held in one hand with the thumb of that one hand in position totally and positively to control the rotor of the mechanism.

It is another object of the present invention to provide such a valving mechanism having a valve body shaped to be securely held by the index and middle fingers with the valve rotor disposed in the space between the index and middle fingers for easy movement by the thumb.

Other objects and features of the present invention will become apparent as this description progresses.

BRIEF DESCRIPTION OF THE DRAWINGS

FIG. 8 shows an alternative rotor control means;

FIG. 9 shows another alternative rotor control means;

FIG. 10 shows yet another embodiment;

FIGS. 16-27 illustrate alternative distal ends of conduit pieces; and

FIGS. 28-30 illustrate a flexible conduit piece, with FIGS. 29 and 30 respectively being views along lines 29a-29a and 30a-30a.

DETAILED DESCRIPTION OF THE DRAWINGS

Figure 1:
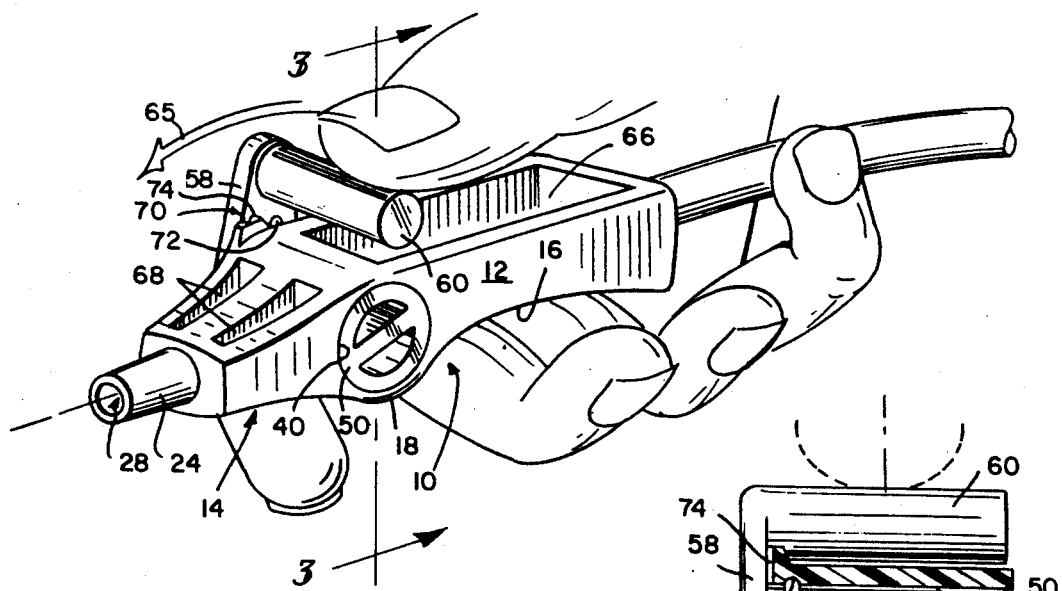
FIG. 1 is a perspective view of the valving mechanism of the present invention showing the mechanism held by one hand with the thumb of the hand controlling the valve rotor.
Figure 3:
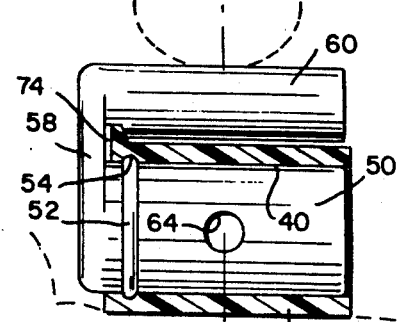
FIG. 3 is a sectional view taken along the lines 3—3 in FIG. 1.

A valving mechanism 10 in accordance with the present invention is shown in perspective view held by a right-hand in FIG. 1. In the drawings, and in this description, like reference numerals represent like parts. The illustrative mechanism 10 is shown comprising a valve body 12 which is illustrated as being a molded plastic, one-piece, elongated valve body molded to have a longitudinally extending body shaped to be gripped and securely held in either hand leaving the hand's thumb free for valve operational movement.

The illustrative valve body 12 is formed at its bottom surface to provide a forward bottom portion 14 shaped to be gripped by the index finger of one hand and a rearward bottom portion 16 shaped to be gripped by the middle finger and, depending upon the size of the hand, by the fourth finger of the hand, with a depending transverse bottom portion 18 between the forward and rearward portions 14, 16. It will be appreciated from the sectional view of FIG. 2 that the recessed portions 14, 16 are smoothly transversely recessed for gripping comfort while the depending central portion 18 is smoothly rounded to fit between the index and middle fingers. It will further be appreciated that, in this description and in the appended claims, statements such as "engaged by the index finger" and "engaged by the middle finger" are intended to indicate the general shape and size of an adult's hand relative to the mechanism 10 and that the body 12 is proportioned and shaped to be held generally by the index and middle fingers pressing the body against the palm of the hand, leaving the thumb free for movement to control the mechanism.

The valve body 12 is further provided with a forward nipple 24 and rearward nipple 26 to which vacuum lines or fluid lines of different types may be connected. These nipples 24, 26 are longitudinally aligned with a passageway 28 formed to extend longitudinally through the valve body 12 when the valve body is molded. The illustrative passageway 28, best seen in FIG. 2, includes a forward passageway portion 30 and a rearward passageway portion 32. In this description and in the appended claims, the term "at least one fluid passageway" is intended to define one or more passageways extending longitudinally through the valve body 12. It will be appreciated, as this description progresses, that the valve body may have, for instance, one, two or even three or more such passageways extending longitudinally therethrough and lying generally in the same plane such that their axes will generally intersect the axis of the valve rotor to be discussed hereinafter. It will further be appreciated that a valve body 12 may be formed to have, for instance, one forward passageway portion 30 and two parallel rearward passageways 32 which may be connected by the valve rotor to be described hereinafter. In summary, concerning the number of passageways, within the scope of the present invention, the valving mechanism 10 may be provided with one or more passageways therethrough and the Passageways may be connected in different combinations by the movement of the rotor.

Figure 2:
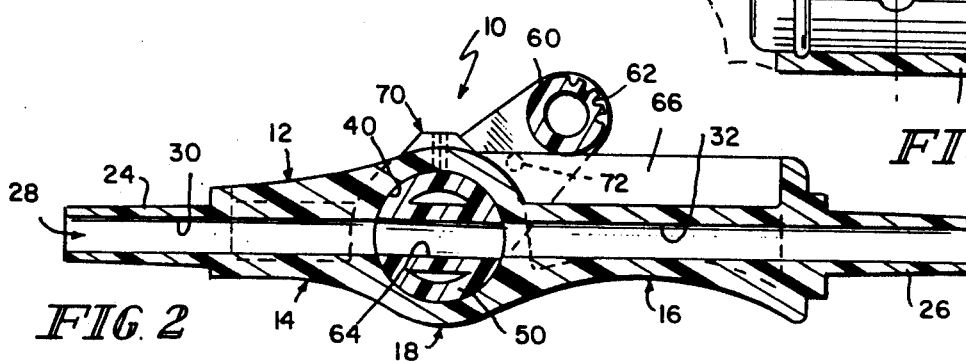
FIG. 2 is a longitudinal sectional view of the mechanism of FIG. 1.

The valve body 12 is molded to provide a cylindrical opening or bore 40 extending transversely through the valve body and illustratively, just above the central body portion 18 which is held between the index and middle fingers of the hand. This cylindrical opening 40 is positioned to intercept the passageway 28 through the valve body as best seen in FIG. 2. A cylindrical, molded plastic, one-piece rotor 50 is snugly and slidably rotatably inserted in the opening 40 to block the passageway 28 except when the rotor is in its passageway opening position.

The body 12 may preferably be molded from a fairly rigid material such as a polycarbonate plastic while the core 50 may preferably be molded from a softer plastic such as a polypropylene, nylon or teflon. The closeness of the snug fit of the rotor 50 in the bore 40 and the nature of the material from which the body 12 and rotor 50 are molded will determine the pressure capacity of the valving mechanism. It will be appreciated that a very snug rotor 50 fit in the bore 40 will accommodate high pressure. The rotor is provided with a peripherally extending ridge 52 integrally molded thereon to be snapped into a groove 54 formed in the bore 40 for the rotor.

Thus, when the softer plastic rotor 50 is inserted into the cylindrical opening or bore 40 so that the ridge 52 engages the groove 54, the valve rotor assembly will be fixed in the valve body 12 to complete the valving mechanism of the illustrative embodiment of FIG. 1. This very simple and easy assembly process is extremely attractive from an assembly cost point of view and from an operational point of view. In the illustrative embodiments of FIGS. 1-6, the rotor 50 is integrally molded and formed to have a one-piece thumb-actuated means for rotating the rotor. That is, as best illustrated in the drawings, the rotor 50 is molded to have a radially upwardly extending connecting portion 58 and a thumb engaging portion 60 extending generally parallel to and above the rotor 50. This engaging portion 60 may be serrated as indicated at 62 to provide a gripping surface for the thumb.

In FIGS. 1-4, the illustrative rotor 50 is provided with a single transaxially extending passageway 64 which is shown in alignment with the passageway portions 30, 32 in FIG. 2. When the rotor is rotated, however, the passageway 28 and its portions 30, 32 will be blocked by the rotor 50. Thus, the rotor 50 rotates between its valve opening position shown in FIG. 2 and a valve closing position 45° removed from that shown in FIG. 2. It will be appreciated that the valve rotor 50 may be moved to its closing position simply by pushing forwardly on the thumb engaging portion 60 as suggested by the arrow 65 in FIG. 1. The valve body 12 may be molded in a conventional fashion to have cavities such as illustrated at 66 and 68 to use less plastic material and to make the valve body lighter and easier to hold. It will also be appreciated that the valve body 12 may be formed with detent means indicated at 70 which will give the medical personnel a feeling for when the rotor 50 is in its desired position. A detent means 70 may include, for instance, a protrusion 72 on the connecting portion 58 of the rotor which must move past a resilient protrusion 74 on the valve body.

Figures 4, 5, 6:
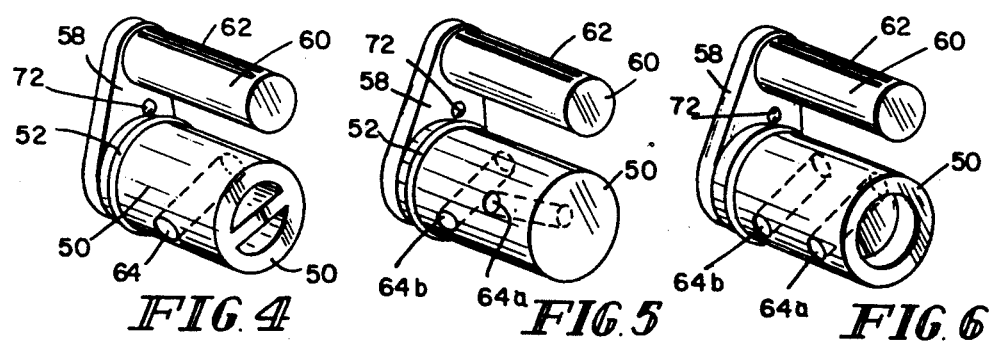
FIGS. 4, 5 and 6 are perspective views of various rotor bodies for the mechanism of FIG. 1.

Referring further to FIGS. 4, 5 and 6, it will be seen that, while FIG. 4 shows a single passageway 64 in the valve rotor 50, FIG. 5 shows transversely spaced apart passageways 64a and 64b which are 90° spaced apart. It will further be seen that FIG. 6 shows two transversely spaced apart passageways 64a and 64b formed in the rotor 50 to accommodate two parallel passageways through the valve body 12. It will be appreciated that, within the scope of this invention, there may be a wide variety of combinations of passageways 64a, 64b with the Passageways arranged to open and close the passageways 28a, 28b at various rotor 50 positions. The passageways 28a, 28b may be opened and closed together or alternately opened and closed. The valve positions of the rotor 50 may be selected to be 45° apart or 90° apart or any selected angle sufficient to provide full closing and opening.

Figure 7:
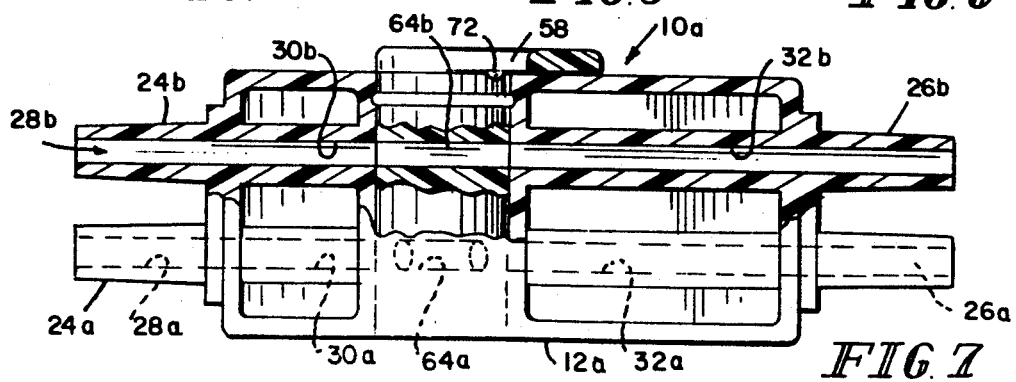
FIG. 7 is a longitudinal sectional view of a different embodiment showing two separate passageways through the valve, both controlled by a valve rotor.

Referring then to FIG. 7, it will be seen that there is illustrated a valving mechanism 10a having a valve body 12a formed to include parallel, side by side, longitudinally extending passageways 28a and 28b. These passageways 28a, 28b are formed to have the forward portions 30a, 30b and rearward portions 32a, 32b connecting, respectively, the forward nipples 24a, 24b and the rearward nipples 26a, 26b. When a rotor such as that illustrated in FIG. 5 is inserted into the valve body 12a of FIG. 7, the passageway 28a is open when the passageway 28b is closed and vice versa. When the rotor assembly of FIG. 6, however, is inserted into the valve body 12a, both passageways 28a, 28b are opened and closed by the same movement of the rotor 50.

In FIG. 8, there is illustrated a valve body having an elongated slot 86 just above the rotor 50, and the rotor 50 is illustrated as having an opening 90 therein for receiving a stem 92 which extends downwardly through the slot 86 to provide a driving connection for the rotor 50. The upper end of this stem 92 carries a crossbar 94 or thumb engaging portion. In the embodiment of FIG. 8, for instance, the stem 92 may be designed to snap into the opening 90 to make a permanent connection between the stem and the rotor 50.

Referring to FIG. 9, it will be seen that another approach for providing a driving connection between the operator's thumb and the rotor 50 is illustrated. In the FIG. 9 structure, the axially outer ends of the rotor 50 are provided with first engaging means 98. A saddle bar 100 is provided for thumb engagement, the saddle bar having depending sides 102, 104 which are formed to provide second engaging means 106 at the lower ends. Illustratively, the first engaging means 98 are male connectors which snap inwardly into the triangularly shaped female connectors of engaging means 106.

Referring to FIG. 10, still another embodiment is shown. In the FIG. 10 embodiment, the valve body has two input passageways 32a, 32b, but only one output passageway 28. (Again, like reference numbers represent like parts.) The rotor 50 in the FIG. 10 embodiment is designed to connect the passageways 26a, 26b alternatively to the passageway 28. Specifically, the passageways 64a, 64b in the rotor 50 connect the passageways 26a, 26b to the passageway 28 depending upon the position of the rotor.

Figure 11:
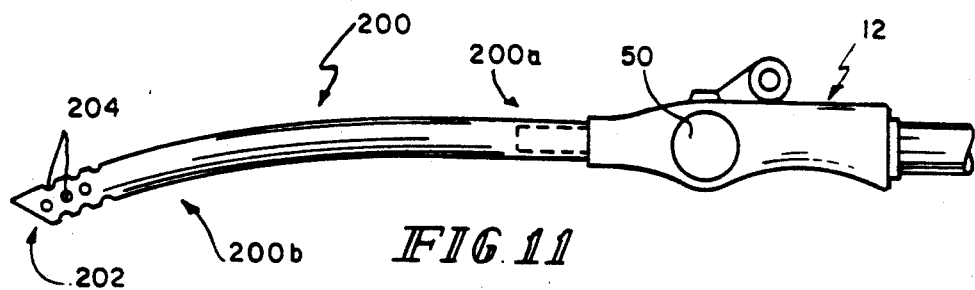
FIG. 11 shows a valve body fitted with a snap-on, friction tight conduit piece that directs fluid leaving the valve body to a conduit piece tip formed to have a plurality of apertures.

FIG. 11 illustrates an embodiment of the invention in which the valve body 12 is fitted with a conduit piece 200 that extends away from the valve body 12 in the valve body 12's direction of elongation before slightly curving downward with respect to the valve body 12. The conduit piece 200 is attached at its proximal end 200a to the valve body 12 and projects outward for interaction with a patients body at its distal end 200b. The amount of fluid introduced into or withdrawn through the conduit piece 200 is controlled by rotation of the rotor 50. Fluid can travel through the conduit piece 200 either toward or away from the valve body 12, respectively depending on whether aspiration or lavage is required. Fluid passing away from the valve body 12 can exit the conduit piece 200 at the terminal outlet 202 and through a plurality of apertures 204 defined in the conduit piece 200.

Figure 12:
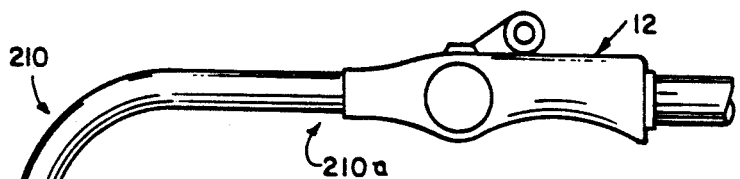
FIG. 12 show the valve body of FIG. 11 fitted with a sharply curving tip useful in dental procedures.

FIG. 12 illustrates the valve body 12 of FIG. 11 connected to a conduit piece 210. The conduit piece 210 sharply curves downward and back toward the valve body 12 so that fluid entering the conduit piece 210 is constrained to reverse its direction of flow before exiting the conduit piece 210 at outlet 212. This is of particular advantage for dental procedures in which portions of the mouth not readily reached by linearly extending or slightly curving conduit pieces such as shown in FIG. 11.

Figure 13:
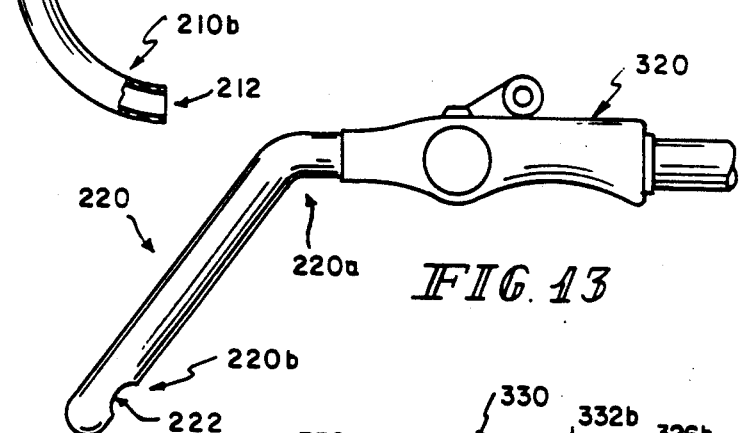
FIG. 13 shows an integrally molded conduit piece and valve body, with the conduit piece being bent to provide a sharply downturning channel for fluid flow relative to the valve body.

FIG. 13 illustrates a sharply downturning conduit piece 220 integrally formed from molded plastic with a valve body 320. Fluid directed through the valve body 320 is directed through the conduit 220 and exits at outlet 222.

Figure 14:
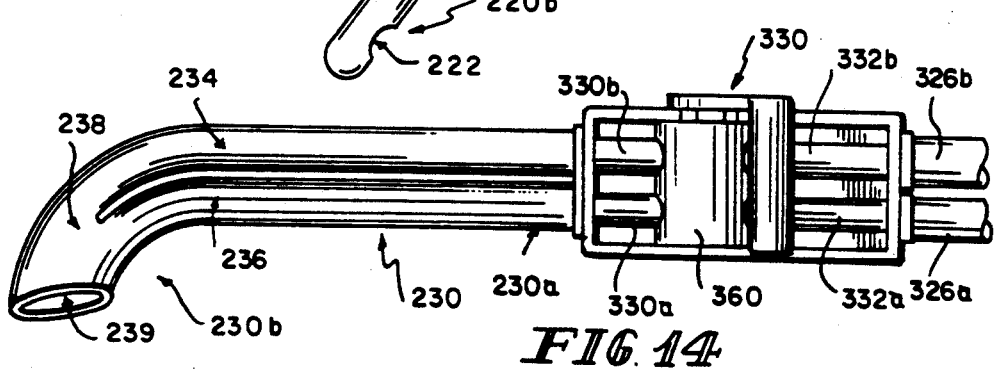
FIGS. 14 and 15 are respectively top and side views of a dual valve having two fluid conduits controlled by a rotor valve, both conduit pieces being configured to curve sideways and downward with respect to the valve body.
Figure 15:
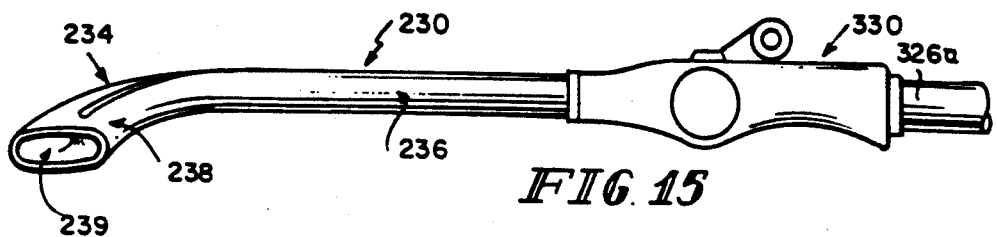

FIGS. 14 and 15 respectively illustrates top and side views of a dual valve 330 connected to a dual conduit piece 230. The dual valve 330 is similar to that shown in FIG. 7 and has a fluid inlet 326b and a vacuum port 326a. Fluid introduced into passageway 332b travels through a passageway (not shown) in the rotor 360 and into a passageway 330b. Fluid leaving the passageway 330b is directed along a curving first conduit piece 234 until it meets with a second conduit piece 236 at a common conduit 238. The fluid can then exit the common conduit 238 at its Port 239.

Fluid can be drawn into the common conduit 238 through the port 239 by connection of the valve body 330 to a vacuum source (not shown). In the embodiment shown, the vacuum source is connected to the vacuum port 326a, and in controlled fluid communication with the common conduit 238 by way of passageways 332a, 330a and conduit piece 236. Application of the vacuum is controlled by the position of the rotor 360 separating the passageways 332a and 330a. The interconnecting passageways (not shown) in the rotor are configured as shown in FIG. 7 so that neither the passageways 330b, 332b or 330a, 332a are simultaneously in fluid communication with each other. This arrangement permits an operator to control both fluid delivery and aspiration with one handed operation.

As illustrated in FIGS. 16–27, the distal end of a conduit piece can include a wide variety of configurations (For example, conduit piece tips 400a through 400f) that are suitable for use in conjunction with single or dual port valves such as respectively shown in FIGS. 10 and FIGS. 14–15. Fluid can be delivered to patients through conduits 410a–410f and withdrawn by aspiration through conduits 420a–420f. Conduits 420a–420f can terminate with a simple opening 430a (conduit 420a); with multiple slots 430b (conduit 400b); with downwardly directed openings 420c (conduit 400c); with multiple sideways directed perforations 430d (conduit 400d); with multiple forward facing perforations 430e (conduit 400e); and with sideways directed slots 430f (conduit 400f).

Figure 28:
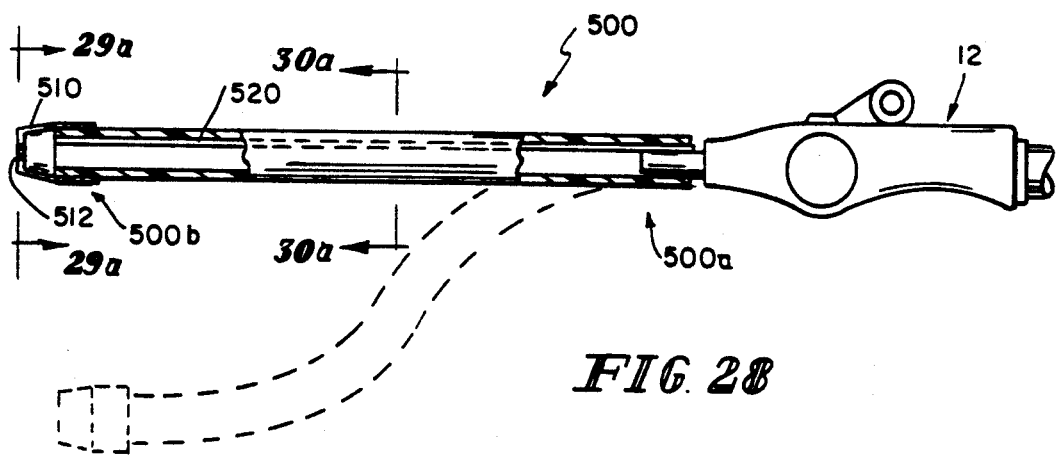
Figure 29:
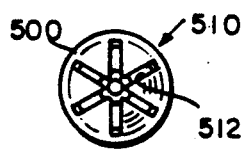
Figure 30:
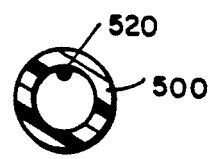

As illustrated in FIGS. 28, 29, and 30, the conduit piece does not have to be formed from a rigid piece snapped-on or integrally molded with the valve body 12. A flexible, resilient polymeric material such as rubber or polyethylene tubing can be formed into a conduit piece 500 (the conduit piece 500 terminates in a tip 510 having forward facing slots 512 to direct fluid flow). As outlined in dotted lines in FIG. 28, the conduit piece 500 can be easily redirected from a first position (in bold lines) so that its distal end 500b is positioned in a predetermined location without requiring movement of its proximal end 500a or attached valve body 12. A semi-rigid support element such as wire 520 can also be coupled to the conduit piece 500 to stabilize the shape of the conduit piece 500, holding it in any desired shape.

The present invention, therefore, provides a disposable, plastic stopcock handle-valve or lavage valving mechanism which a user can hold and operate with either hand. The body of the handle-valve has a contoured bottom surface that fits into enough of the palm side of either hand of the operator, starting with the index finger, to permit the operator to both operate the handle-valve and direct its motion. Importantly, for control purposes, the thumb engages an actuating means which is preferably disposed axially and longitudinally just above the rotor of the valve, and this actuating or engaging portion may be integrally molded with the rotor. For control purposes, the connecting portion 58 of the rotor assembly may have a moment-arm of approximately one-inch and a stroke of approximately three-fourths inch, a comfortable span for either an adult female or male hand. The top extension of the thumb engaging portion may be serrated to facilitate its movement by the thumb and the bottom or other surfaces of the valve body may be serrated at convenient locations to provide a convenient and comfortable grip. The valve body 12 and the core 50 are assembled with a slight interference fit to provide a good seal between the body and the core without requiring extreme pressure in excess of that which is comfortable for an adult female or male to move by thumb action. A conduit piece is attached to the valve body in fluid communication said fluid passageway extending longitudinally through the valve body. This conduit piece has a proximal end attached to the valve body and a distal end projecting outward from the valve body for patient contact, and introduction of fluid into the conduit piece is controlled by rotation of the rotor with the thumb actuated controls.

What is claimed is:

1. A hand-held lavage mechanism comprising
an elongated valve body configured to have a longitudinally extending body shaped to be gripped and securely held in either hand while leaving the hand's thumb free for valve operational movement, said body providing at least one fluid passageway extending longitudinally therethrough from one end of the body to another end, said body also providing a cylindrical opening extending transversely therethrough and intercepting said at least one passageway, a cylindrical molded plastic, one-piece rotor having smooth cylindrical sides inserted into said cylindrical opening for snug slidable and rotational contact with sides of said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, and thumb-actuated means for rotating said rotor, said actuated means being attached to said rotor and disposed above said valve body and said rotor for convenient thumb movement of said rotor while the valve body is gripped and held by the hand, and
a conduit piece attached to the valve body in fluid communication said fluid passageway extending longitudinally through the valve body, said conduit piece having a proximal end attached to said valve body and a distal end projecting outward from said valve body for patient contact, and wherein rotation of said rotor controls introduction of fluid into the conduit piece.

2. The mechanism of claim 1 in which said conduit piece is formed to curve downward with respect to the valve body.

3. The mechanism of claim 2 in which said conduit piece is formed to curve sideways with respect to the valve body.

4. The mechanism of claim 1 in which said conduit piece is formed from a flexible polymeric material that can be reoriented to direct the distal end of the conduit piece to a predetermined location without requiring movement of the valve body.

5. The mechanism of claim 4 wherein a semi-rigid support element is coupled to the flexible conduit piece so that the flexible conduit piece remains in position after reorientation of the flexible conduit piece.

6. A hand-held lavage mechanism comprising
an elongated valve body configured to have a longitudinally extending body shaped to be gripped and securely held in either hand while leaving the hand's thumb free for valve operational movement, said body providing at least one fluid passageway extending longitudinally therethrough from one end of the body to another end, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one fluid passageway therethrough which opens said at least one fluid passageway through said valve body when said rotor is in said valve opening position and which closes said at least one fluid passageway when said rotor is in said valve closing position, and thumb-actuated means for rotating said rotor, said actuated means being attached to said rotor and disposed above said valve body and said rotor for convenient thumb movement of said rotor while the valve body is gripped and held by the hand, and
a conduit piece attached to the valve body in fluid communication said fluid passageway extending longitudinally through the valve body, said conduit piece having a proximal end attached to said valve body and a distal end projecting outward from said valve body for patient contact, and wherein rotation of said rotor controls introduction of fluid into the conduit piece, and in which said valve body is molded to have a first bottom portion shaped to be gripped by the index finger of one hand and a second bottom portion shaped to be gripped by the middle finger of the hand with a third depending transverse bottom portion between said forward and rearward portions, said third depending transverse bottom portion being directly below said cylindrical opening which holds said rotor to be disposed partially between the index and middle fingers for stabilization with the fingers holding the body against the palm of the hand.

7. The mechanism of claim 2 in which said second bottom portion is transversely recessed to provide a comfortable gripping surface and said thumb-actuated means includes a molded-plastic saddle bar extending transversely across said valve body above said rotor with integrally formed side bars depending from said saddle bar ends and drivingly connected to said rotor.

8. A hand-held lavage mechanism comprising an elongated valve body configured to have a longitudinally extending body shaped to be gripped and securely held in either hand while leaving the hand's thumb free for valve operational movement, said body providing at least one fluid passageway extending longitudinally therethrough from one end of the body to another end, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, and thumb-actuated means for rotating said rotor, said actuated means being attached to said rotor and disposed above said valve body and said rotor for convenient thumb movement of said rotor while the valve body is gripped and held by the hand, and a conduit piece attached to the valve body in fluid communication said fluid passageway extending longitudinally through the valve body, said conduit piece having a proximal end attached to said valve body and a distal end projecting outward from said valve body for patient contact, and wherein rotation of said rotor controls introduction of fluid into the conduit piece, and wherein said conduit piece includes a first conduit piece in fluid communication with a first longitudinally extending passageway formed in the valve body, a second conduit piece in fluid communication with a second longitudinally extending passageway formed in the valve body, and a distally located, patient contacting common conduit in fluid communication with both the first and second conduit pieces as controlled by the valve rotor so that fluid introduced through the first conduit piece into a patient's body can be withdrawn by suction applied through the second conduit piece.

9. A medical device valving mechanism comprising an elongated valve body molded to have a longitudinally extending body shaped to be gripped and securely held in a user's hand leaving the hand's thumb free for valve operational movement, said body providing at least one fluid passageway extending longitudinally therethrough from one end of the body to another end, said body also providing a cylindrical opening extending transversely therethrough and intercepting said at least one passageway, a cylindrical molded plastic, one-piece rotor having smooth cylindrical sides inserted into said cylindrical opening for snug slidable and rotational contact with sides of said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, and thumb-actuated means connected to said rotor for rotating said rotor, said actuated means being disposed above said valve body and said rotor for convenient thumb movement of said rotor, and wherein the shaped body is gripped and held by fingers of the user's hand at points located on the shaped body below ends of said transaxial passageway of the rotor with the fingers of the user's hand being located below the thumb-actuated means so as to provide the free thumb for valve operational movement, and a conduit piece attached to the valve body in fluid communication said fluid passageway extending longitudinally through the valve body, said conduit piece having a proximal end attached to said valve body and a distal end projecting outward from said valve body for patient contact, and wherein rotation of said rotor controls introduction of fluid into the conduits piece.

10. The mechanism of claim 9 in which said conduit piece is formed to curve downward with respect to the valve body.

11. The mechanism of claim 10 in which said conduit piece is formed to curve sideways with respect to the valve body.

12. A medical device valving mechanism comprising an elongated valve body configured to have a longitudinally extending body shaped to be gripped and securely held in a users hand leaving the hand's thumb free for valve operational movement, said body providing at least one fluid passageway extending longitudinally therethrough from one end of the body to another end, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, and wherein the shaped body is gripped and held by fingers of the user's hand at points located on the shaped body below ends of said transaxial passageway of the rotor with the fingers of the user's hand being located below the thumb-actuated means so as to provide the free thumb for valve operational movement, and
- a conduit piece attached to the valve body in fluid communication said fluid passageway extending longitudinally through the valve body, said conduit piece having a proximal end attached to said valve body and a distal end projecting outward from said valve body for patient contact, and wherein rotation of said rotor controls introduction of fluid into the conduits piece, wherein said conduit piece includes a first conduit piece in fluid communication with a first longitudinally extending passageway formed in the valve body, a second conduit piece in fluid communication with a second longitudinally extending passageway formed in the valve body, and a distally located, patient contacting common conduit in fluid communication with both the first and second conduit pieces as controlled by the valve rotor so that fluid introduced through the first conduit piece into a patient's body can be withdrawn by suction applied through the second conduit piece.

13. A medical device valving mechanism comprising an elongated valve body molded to have a longitudinally extending body shaped to be gripped and securely held in a users hand leaving the hand's thumb free for valve operational movement, said body providing at least one fluid passageway extending longitudinally therethrough, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, wherein said valve body is molded to have a first bottom portion shaped to be gripped by the index finger of one hand and a second bottom portion shaped to be gripped by the middle finger of the hand with a third depending transverse bottom portion between said first and second portions, said transverse bottom portion being directly below said cylindrical opening which holds said rotor to be disposed partially between the index and middle fingers for stabilization with the fingers holding the body against the palm of the hand, and
- a conduit piece attached to the valve body in fluid communication said fluid passageway extending longitudinally through the valve body, said conduit piece having a proximal end attached to said valve body and a distal end projecting outward from said valve body for patient contact, and wherein rotation of said rotor controls introduction of fluid into the conduit piece.

14. The mechanism of claim 13 wherein said thumb-actuated means includes a molded-plastic saddle bar extending transversely across said valve body above said rotor with integrally formed side bars depending from said saddle bar ends and drivingly connected to said rotor, the side bars are drivingly connected through first engaging means on opposite ends of the rotor which extend outwardly from said valve body and wherein said side bars are provided with second engagement means for snapping engagement respectively with said first engagement means.

* * * * *